US006907796B2

(12) United States Patent
Bremer et al.

(10) Patent No.: US 6,907,796 B2
(45) Date of Patent: Jun. 21, 2005

(54) TEMPERATURE-CONTROLLED INJECTOR FOR A CHEMICAL ANALYSIS UNIT

(75) Inventors: Ralf Bremer, Oberhausen (DE); Bernhard Rose, Dusseldorf (DE)

(73) Assignee: Gerstel Systemtechnik GmbH & Co. KG (DE)

( * ) Notice: Subject to any disclaimer, the term of this patent is extended or adjusted under 35 U.S.C. 154(b) by 398 days.

(21) Appl. No.: 10/143,722

(22) Filed: May 9, 2002

(65) Prior Publication Data

US 2004/0159167 A1 Aug. 19, 2004

(30) Foreign Application Priority Data

May 30, 2001 (DE) .......................... 101 26 231
Jun. 23, 2001 (DE) .......................... 101 30 382

(51) Int. Cl.$^7$ .......................... G01N 30/02; G01N 30/30
(52) U.S. Cl. .................. 73/863.11; 73/19.02; 73/23.35; 73/61.52; 95/87; 219/628; 219/630; 219/632
(58) Field of Search .......................... 73/19.02, 23.35, 73/23.39, 23.41, 23.42, 62.52, 61.53, 61.55, 863.11, 864.81, 864.85, 864.91; 95/82, 83, 84, 85, 86, 87, 88; 219/600, 628, 630, 631, 632

(56) References Cited

U.S. PATENT DOCUMENTS 4,019,863 A * 4/1977 Jenkins et al. .............. 250/304
4,096,908 A * 6/1978 Lamy .......................... 165/64

(Continued)

FOREIGN PATENT DOCUMENTS

| DE | 3400458 A1 | * 7/1985 | .......... G01N/30/18 |
| DE | 198 10 109 A1 | 10/1999 | |
| DE | 19810109 A1 | * 10/1999 | .......... G01N/30/18 |
| DE | 19817016 A1 | * 10/1999 | .......... G01N/30/04 |
| DE | 198 17 017 A1 | 10/1999 | |
| JP | 11295285 A | * 10/1999 | .......... G01N/30/16 |
| JP | 2002-141 767 | 5/2002 | |
| RU | 2137260 C1 | * 9/1999 | ........... F25B/21/02 |

OTHER PUBLICATIONS

Cubberly, William H., "SAE Dictionary of Aerospace Engineering", 1992, Society of Automotive Engineers, Inc., p. 40.*

Mark Klemp et al., "Sample Decomposition in an Electrically Heated Cold–Trap Inlet System for High Speed Gas Chromatography," *Journal of High Resolution Chromatography*, vol. 14, Apr. 1981 (pp. 235–240).

Stephen R. Springston, "Cryogenic–focusing, ohmically heated on–column trap for capillary gas chromatography," *Journal of Chromatography*, 517 (1990), pp. 67–75.

*Primary Examiner*—Hezron Williams
*Assistant Examiner*—David A. Rogers
(74) *Attorney, Agent, or Firm*—Patterson, Thuente, Skaar & Christensen, P.A.

(57) ABSTRACT

The invention relates to a temperature-controlled injector for a chemical analysis unit, in particular a gas chromatograph, comprising an injector tube, which can be received by a receiving tube, having a cooling system, which surrounds the receiving tube, through which coolant can flow, which has coolant connections and which is designed as a metallic tube coil, and a resistance heating system for the injector tube, in which injector the receiving tube consists of a material of good thermal conductivity, is electrically insulating towards the outside, and the tube coil rests on the receiving tube, has an electrical resistance which is sufficient to rapidly heat the injector tube and can be acted on by current via electrical connection pieces.

13 Claims, 3 Drawing Sheets

U.S. PATENT DOCUMENTS

| | | | |
|---|---|---|---|
| 4,668,261 A | * 5/1987 | Chatzipetros et al. | 62/55.5 |
| 4,766,760 A | * 8/1988 | Poshemansky et al. | 73/23.35 |
| 4,861,989 A | * 8/1989 | Vestal et al. | 250/288 |
| 5,410,134 A | * 4/1995 | Marcut et al. | 219/676 |
| 5,588,988 A | * 12/1996 | Gerstel et al. | 96/101 |
| 5,686,656 A | * 11/1997 | Amirav et al. | 73/23.41 |
| 5,778,681 A | * 7/1998 | Li et al. | 62/50.2 |
| 5,954,860 A | * 9/1999 | Gordon | 95/87 |
| 6,054,683 A | * 4/2000 | Bremer et al. | 219/388 |
| 6,055,845 A | * 5/2000 | Gerstel et al. | 73/23.42 |
| 6,093,371 A | * 7/2000 | Wilson | 422/89 |
| 6,134,945 A | * 10/2000 | Gerstel et al. | 73/23.42 |
| 6,498,042 B1 | * 12/2002 | Wilson | 436/174 |

* cited by examiner ic injector for a chemical analysis unit like a gas chromatograph. Such an injector is used to introduce samples to be analysed into a chemical analysis unit.

BACKGROUND OF THE INVENTION

From German Patent DE 198 10 109 C2 an injector for a chemical analysis unit, such as a gas chromatograph, which can be heated by means of a heater device in accordance with a predetermined temperature profile and can be cooled by means of a cooling device which concentrically surrounds the heater device, is known. The cooling device is in this case designed as a cooling hose which is arranged on a shell into which an injector tube can be fitted, with the heater device, for instance in the form of a heater cartridge, approximately as described in German Patent DE 198 17 017 C2. Apart from the fact that, in this design, there is a considerable outlay on assembly, the cycle times of the gas chromatograph are also correspondingly limited by the cooling and heating cycles required.

However, a temperature-controlled injector can also be used in combination with a thermodesorption device, as described, for example, in German Patent DE 196 53406 C1, or in combination with a desorption device which incorporates a manifold, as described in German Patent DE 199 13 809 A1.

SUMMARY OF THE INVENTION

It is an object of the invention to provide a temperature-controlled injector which is of simplified structure and to provide a temperature-controlled injector which allows higher cycle times of a gas chromatograph to be achieved.

Thus, there is provided a temperature-controlled injector for a chemical analysis unit, comprising:

an injector tube; and a receiving tube for receiving the injector tube;

wherein the receiving tube comprises a cooling system, which surrounds the receiving tube, through which coolant can flow, which has coolant connections and which is designed as a metallic tube coil; and a resistance heating system for the injector tube;

wherein the receiving tube consists of a material of good thermal conductivity and is electrically insulating towards the exterior; and wherein the tube coil rests on the receiving tube, has an electrical resistance which is sufficient to rapidly heat the injector tube and is provided with connection pieces for connecting it to a current source.

An injector of this type, in which the cooling coil is simultaneously designed as a resistance heater coil, allows rapid cycle times to be achieved by rapid heating and rapid cooling, resulting in a widened range of applications in particular in gas chromatography. Rapid heating means that premature separation in the injector is virtually eliminated. When switching from cooling to heating, the liquid coolant contained in the tube coil is rapidly heated and, if appropriate, evaporated.

The tube coil which is used as the cooling coil and resistance heater must have a sufficient electrical resistance to rapidly heat the injector, i.e. its resistance must not be so low that the current intensity rises to such an extent that it cannot be delivered using a commercially available transformer. Accordingly, the current intensity should preferably be limited to approximately 50 A, in particular approximately 15 A.

The injector can be used, inter alia, for cold injection systems, thermodesorption systems, traps used in gas chromatographs, and also in injection systems for analysis units such as mass spectrometers or interconnected gas chromatographs.

Further objects, embodiments and advantages of the invention are given in the following description.

BRIEF DESCRIPTION OF THE DRAWINGS

The invention is explained in more detail below with reference to exemplary embodiments which are illustrated in the appended drawings, in which.

DETAILED DESCRIPTION OF PREFERRED EMBODIMENTS

Figure 1:
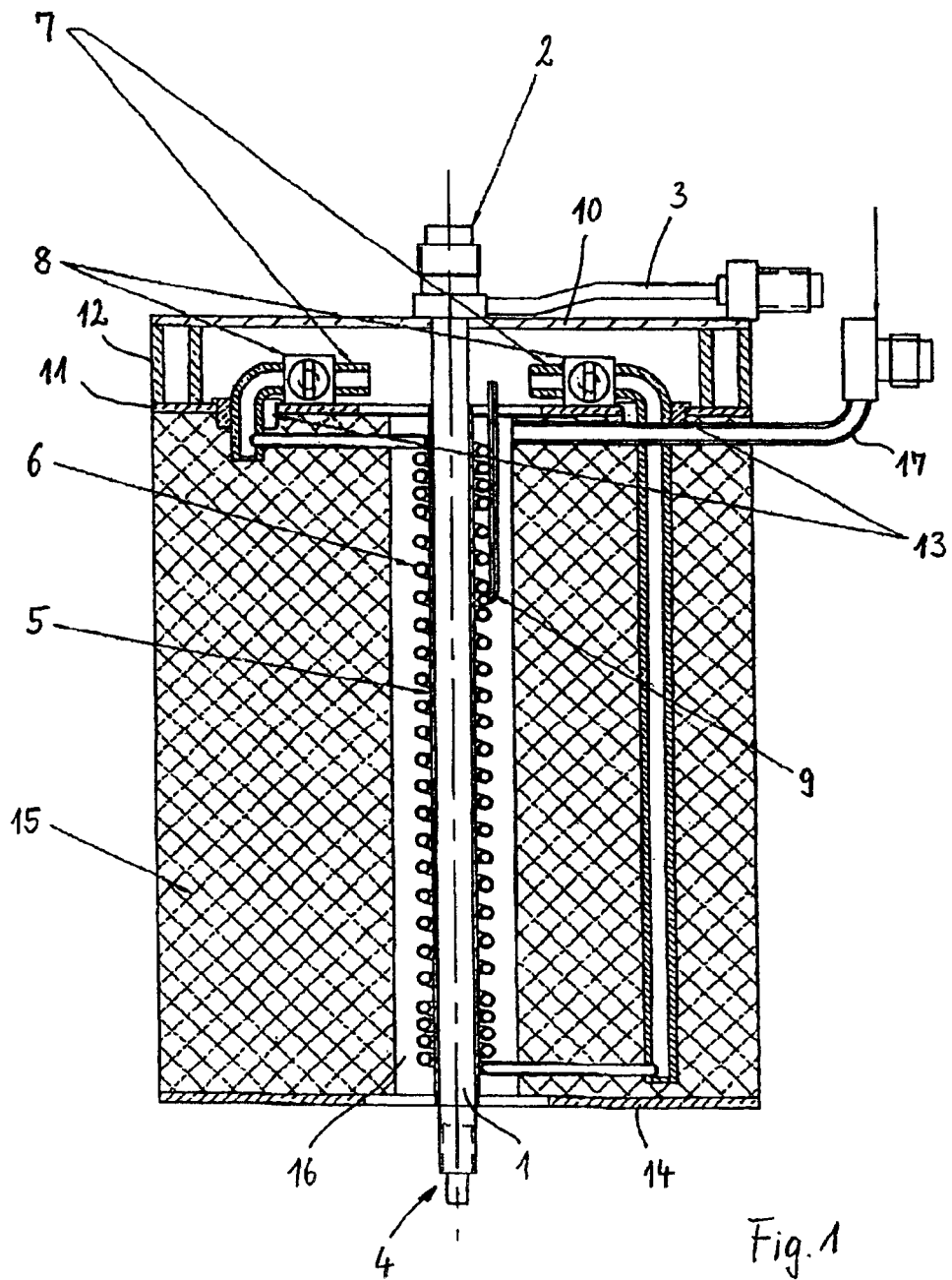
FIG. 1 shows a sectional view through an embodiment of a temperature-controlled injector.

The injector which is illustrated in FIG. 1 comprises an injector tube 1 having an end piece 2 which is provided with a carrier-gas connection 3. At the end which is remote from the end piece 2, the injector tube 1 has a connection 4 for connection to a capillary column of a gas chromatograph.

The injector tube 1 is used, for example, in a cold injection device for a gas chromatograph to receive a sample injection tube which is provided with a liner in order to adsorb substances which are injected into the sample injection tube, for example using an injection needle, and are to be tested, in the cooled state, and then to release these substances into a carrier-gas stream, for example into a stream of nitrogen, by heating of the sample injection tube and to feed them to the capillary column with or without a split.

The injector tube 1 fits snugly inside a metallic receiving tube 5, which is provided on its outer side with an electrically insulating oxide layer. It is preferably a tube made from an aluminium alloy which is hard-anodized on the outer side.

As an alternative to a metal tube, the receiving tube 5 may also be a tube made from another material of good thermal conductivity which is also electrically insulating, for example a suitable ceramic material.

A tube coil 6 rests on the receiving tube 5. The tube coil 6 comprises a very thin-walled, small-diameter tube. The tube coil 6 comprises, for example, a stainless-steel tube with a diameter of approximately 0.8 to 3 mm, for example 1.3 mm, and a wall thickness in the region of a fraction of a millimetre, for example of 0.1 mm.

The ends of the tube coil 6 are connected to coolant connections 7 which are formed from pieces of tube and have a greater diameter, in the region of a few millimetres, and consist of a metal of good conductivity, such as copper or the like. The coolant connections 7, which are connected to a coolant source (not shown) of a coolant circuit, for example by corresponding hoses, bear electrical connection piece 8.

Depending on the particular application, the coolant source may be a reservoir for liquid coolant, such as water or coolant oil, which is cooled, for example, by means of a Peltier element or a fan-cooled condenser when the tube coil 6 is used as an evaporator, and is circulated by means of a pump. A temperature of approximately −70° C. can be reached by means of cryostatic cooling of this type.

The metallic contact between the tube coil 6 and the receiving tube 5 and between the latter and the injector tube 1 results in effective cooling of the latter.

The electrical connection pieces 8 can be connected to a current source (not shown), so that a current can flow through the tube coil 6 via the coolant connections 7, i.e. the tube coil 6 simultaneously forms a resistance heating means. This requires the narrow wall thickness of the tube which is used for the tube coil and a sufficient resistivity of the material used for the tube, such that a power of >100 Watts, preferably >120 Watts, is supplied in particular at a voltage of <40 V, in particular at a voltage of <24 V. Therefore, examples of suitable materials are stainless steel, Inconel or the like, while copper or silver would have an excessively high conductivity.

If voltages of <40 V are used, the injector is covered by the low-voltage guideline, and consequently the outlay on circuitry is correspondingly reduced and earthing is not required. This applies in particular when a voltage of $\leq 24$ V is used.

In the region of the tube coil 6 there is a thermocouple 9, by means of which the resistance heating can be controlled in accordance with a desired heating profile by means of a control unit (not shown).

The end piece 2 is secured to a plate 10 which is arranged parallel to a further plate 11, which has a central passage opening, the two plates 10, 11 being separated from one another by spacers 12. Angled-off ends of the coolant connections 7, which are guided through the plate 11 via insulating bushes 13, for example consisting of hard-anodized aluminium, open out into the region between the two plates 10, 11, where they bear the electrical connection pieces 8.

The electrical connection pieces 8 may be clamps to which suitable connection wires (not shown) are secured.

The connection wires may also be soldered directly to the coolant connections 7. It is also possible to use ceramic bar terminals in order to electrically connect the connection wires to the coolant connections 7.

At a distance from the plate 11 there is a further plate 14, which has a central passage opening, in the region of the connection 4, an insulating block 15 made from thermally insulating material being arranged between the plates 11 and 14. The ends of the tube coil 6 and the corresponding sections of the coolant connections 7 are embedded in the insulating block 15.

Liquefied gas, such as nitrogen or carbon dioxide, by means of which it is possible to reach lower temperatures than with cryostatic cooling, cannot be conveyed through the tube coil 6, on account of the high resistance. Therefore, if lower temperatures are to be reached, this can be achieved by allowing liquefied gas to flow through the interspace 16 between insulating block 15 and the receiving tube 5 with the tube coil 6 arranged thereon, via suitable connections 17 (of which one is illustrated).

The tube coil 6 is expediently initially preformed on a mandrel, the diameter of which is slightly smaller than that of the receiving tube 5, so that the tube coil 6 fits suitably to the receiving tube 5.

The tube coil 6 may be wound more tightly at both ends than in the central region, in order to achieve a temperature distribution which is as uniform as possible.

The receiving tube 5 may also be a tube which is provided on its outer circumference with a groove for insertion of the tube coil 6.

Figure 2:
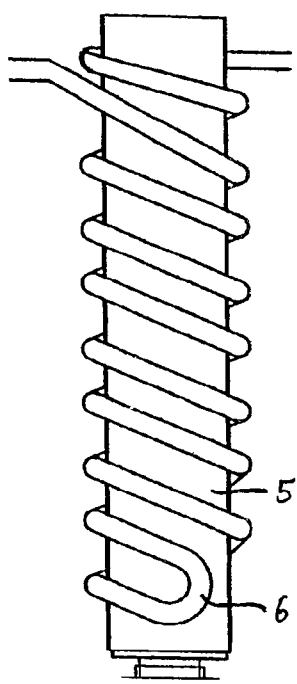
FIGS. 2 and 3 show two alternatives for cooling coil windings for the injector shown in FIG. 1.
Figure 3:
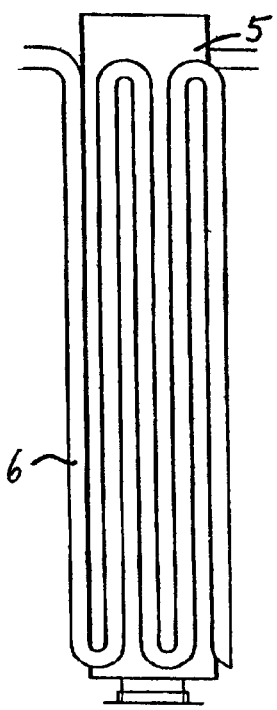

The tube coil 6 may also, as illustrated in FIGS. 2 and 3, be wound in bifilar or meandering form, with the result that its inlet and outlet ends are located in an adjacent region.

Figure 4:
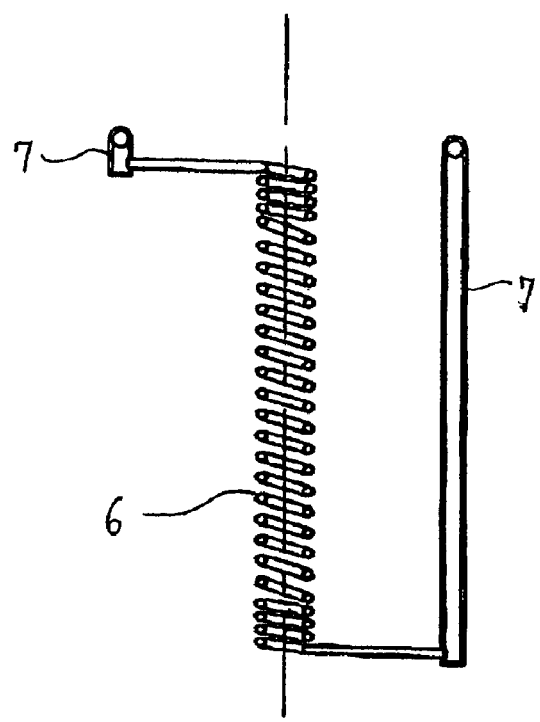
FIGS. 4 and 5 show a tube coil for the injector shown in FIG. 1 with an embodiment of its electrical connections.
Figure 5:
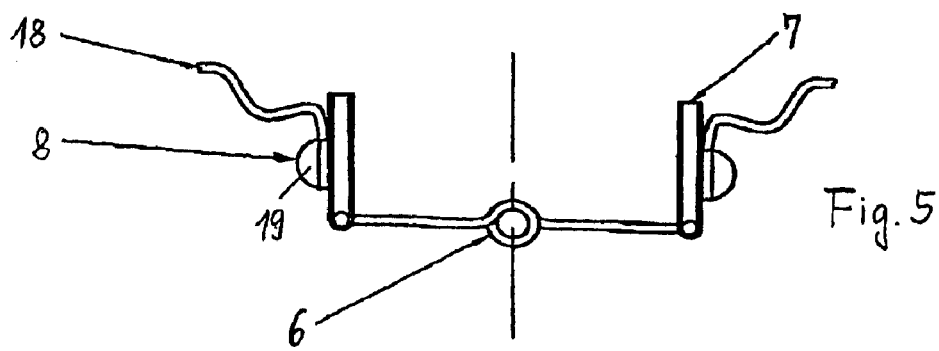

FIG. 4 shows a side view of the tube coil 6 with its coolant connections 7, while FIG. 5 shows a plan view of FIG. 4 with the associated electrical connection pieces 8. One end of an electrical connection cable 18 is connected to the copper tube of the respective coolant connection 7 by brazing at a brazing point 19.

Figure 6:
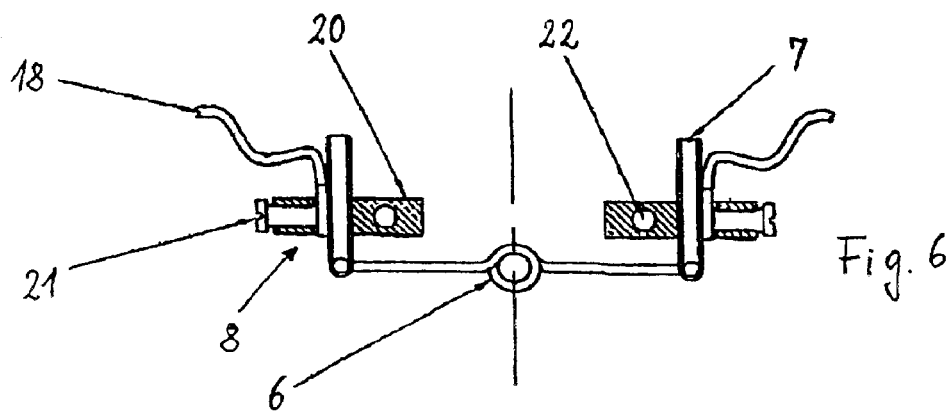
FIG. 6 shows a tube coil for the injector shown in FIG. 1 with a further embodiment of its electrical connections.

By contrast, in the embodiment illustrated in FIG. 6, an electrical connection terminal 20, for example made from ceramic, is arranged on the corresponding copper tube of the respective coolant connection 7, this terminal receiving a clamping screw 21 which clamps one end of the connection cable 18 to the copper tube and therefore also the electrical connection terminal 20, which is provided with at least one mounting hole 22.

While the invention has been shown and described with reference to the preferred embodiments, it should be apparent to one ordinary skilled in the art that many changes and modifications may be made without departing from the spirit and scope of the invention as defined in the claims.

What is claimed is:

1. A temperature-controlled injector for a chemical analysis unit comprising:
   an injector tube; and
   a receiving tube for receiving the injector tube;
   wherein the receiving tube comprises a cooling system which surrounds the receiving tube, through which coolant can flow, which as coolant connections and which is designed as a metallic tube coil; and a resistance heating system for the injector tube;
   wherein the receiving tube comprised of thermally conductive material and is electrically insulating towards the exterior; and
   wherein the tube coil rests on the receiving tube, has an electrical resistance which is sufficient to rapidly heat the injector tube by thermal conduction and is provided with pieces for connecting it to a current source.

2. The injector according to claim 1, wherein the receiving tube is a metal tube and on the outer side has an electrically insulating oxide layer.

3. The injector according to claim 1, wherein the receiving tube is an anodized tube made from an aluminium alloy.

4. The injector according to claim 1, wherein the tube coil fits to the receiving tube.

5. The injector according to claim 1, wherein the tube coil supplies an output of >100 Watts at a voltage of <40 V.

6. The injector according to claim 1, wherein the tube coil is a stainless steel tube with a diameter in the range from approximately 0.8 to 3 mm.

7. The injector according to claim 1, wherein the tube coil is a stainless-steel tube with a wall thickness of a fraction of a millimetre.

8. The injector according to claim 1, wherein the coolant connection pieces are pieces of tube made from a metal of good conductivity which bear electrical connection terminals.

9. The injector according to claim 1, wherein the injector tube is surrounded by a heat-insulating block in the section which bears the tube coil.

10. The injector according to claim 9, wherein an interspace, through which coolant can flow, is provided between the tube coil and the heat-insulating block.

11. The injector according to claim 1, wherein the tube coil is wound in bifilar or meandering form.

12. The injector according to claim 1, wherein electrical connection cables are soldered to the coolant connections.

13. The injector according of claim 1, wherein electrical connection cables are clamped to the coolant connections by means of electrical connection terminals.

* * * * *